Figure 1:
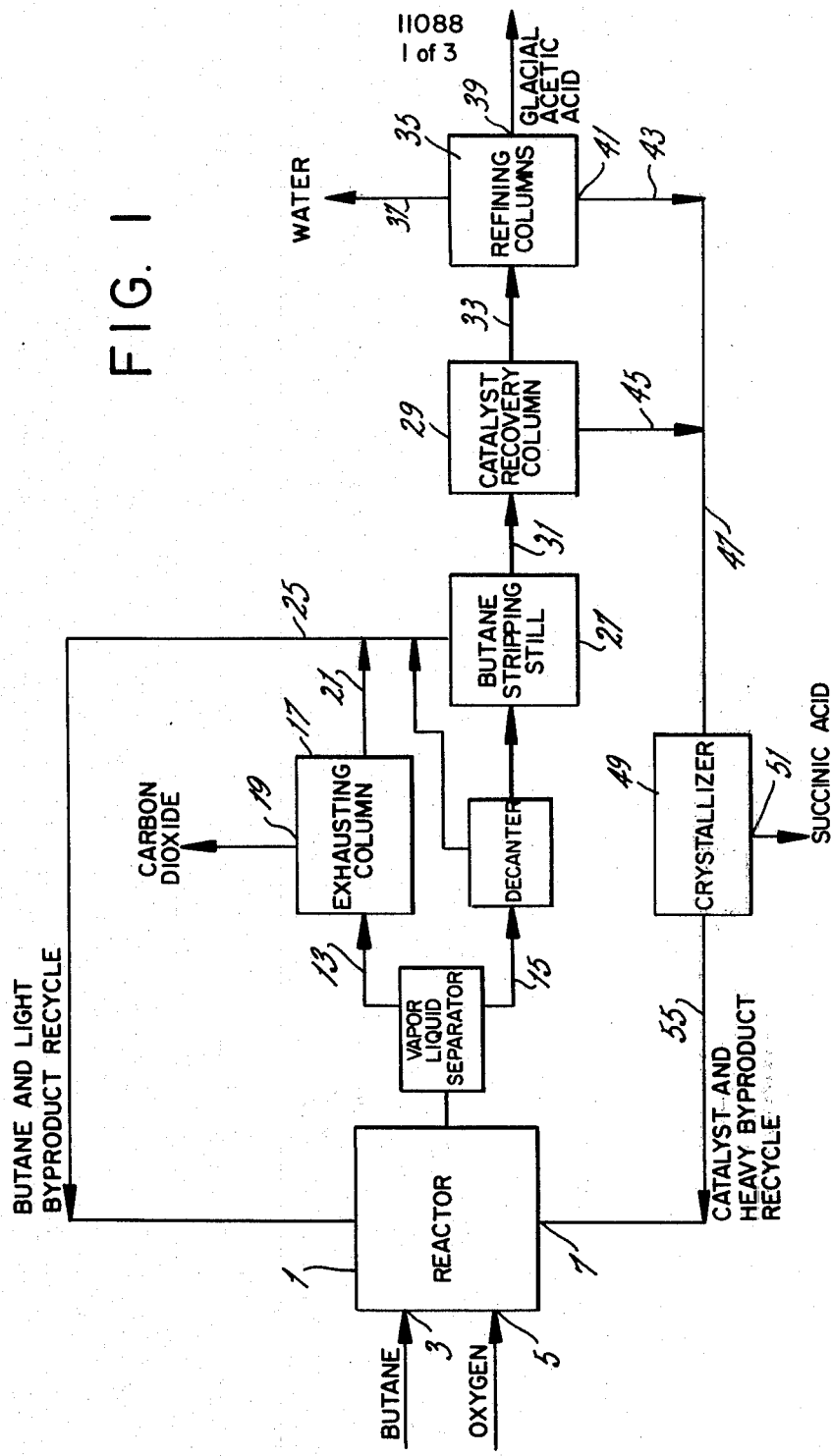

United States Patent [19]

Logsdon et al.

[11] 4,337,356

[45] Jun. 29, 1982

[54] CATALYTIC LIQUID-PHASE OXIDATION OF BUTANE

[75] Inventors: John E. Logsdon; Ben W. Kiff, So. Charleston, both of W. Va.

[73] Assignee: Union Carbide Corporation, Danbury, Conn.

[21] Appl. No.: 132,298

[22] Filed: Mar. 20, 1980

[51] Int. Cl.³ .................... C07C 51/215; C07C 53/08; C07C 55/10

[52] U.S. Cl. .................... 562/549; 562/593; 562/608

[58] Field of Search .................... 562/549, 593, 608

[56] References Cited

U.S. PATENT DOCUMENTS

| | | | |
|---|---|---|---|
| 2,265,948 | 12/1941 | Loder | 562/549 |
| 2,704,294 | 3/1955 | Morgan et al. | 562/549 |
| 3,293,292 | 12/1966 | Olivier et al. | 562/549 |
| 3,483,250 | 12/1969 | Sugarman | 562/549 |
| 3,644,512 | 2/1972 | Onopchenko et al. | 562/549 |
| 3,646,128 | 2/1972 | Cox et al. | 562/549 |
| 3,840,469 | 10/1974 | Hobbs et al. | 562/549 |
| 3,904,675 | 9/1975 | Saunby | 562/549 |
| 3,923,882 | 12/1975 | Kiff | 562/549 |
| 4,032,570 | 6/1977 | Schulz et al. | 562/549 |
| 4,052,417 | 10/1977 | Slinhard et al. | 562/549 |
| 4,086,267 | 4/1978 | Bartlett et al. | 562/549 |
| 4,131,741 | 12/1978 | Bartlett et al. | 562/549 |
| 4,131,742 | 12/1978 | Hudson | 562/549 |

FOREIGN PATENT DOCUMENTS

| | | | |
|---|---|---|---|
| 875586 | 7/1971 | Canada | 562/549 |
| 975710 | 11/1964 | United Kingdom | 562/549 |
| 1197790 | 7/1970 | United Kingdom | 562/549 |

OTHER PUBLICATIONS

Hackh's Chemical Dictionary, p. 298, 1969, 4th Ed.

*Primary Examiner*—Vivian Garner
*Attorney, Agent, or Firm*—Bernard F. Crowe

[57] ABSTRACT

The continuous cobalt catalyzed liquid-phase oxidation of butane to acetic acid with oxygen has been improved by limiting the amount of iron, water and succinic acid present and maintaining a minimum of about 0.1% of cobalt acetate catalyst in the reaction medium.

5 Claims, 3 Drawing Figures

CATALYTIC LIQUID-PHASE OXIDATION OF BUTANE

BACKGROUND OF THE INVENTION

This invention pertains to the continuous cobalt-catalyzed, liquid-phase oxidation of butane with oxygen and more particularly to the improvement of this process by limiting the amount of iron, water, and succinic acid by-product present while maintaining a minimum amount of cobalt acetate as a catalyst in the reaction mixture.

The oxidation of butane is a well-known process which has been described in numerous patents and technical publications relating to both liquid phase and vapor phase oxidation both catalytically and noncatalytically. U.S. Pat. No. 3,646,128 discloses an uncatalyzed butane oxidation process.

U.S. Pat. No. 3,923,882 discloses a butane oxidation process which utilizes ethanol as a promoter for the oxidation. U.S. Pat. No. 2,265,948 teaches a method of oxidizing normally gaseous saturated hydrocarbons in a liquid phase utilizing acetaldehyde as an initiator. U.S. Pat. No. 4,032,570 discloses a liquid phase process for converting butane to acetic acid with molecular oxygen and a cobalt catalyst while maintaining in the reaction zone all of the components of the reaction mixture including the water of reaction throughout the reaction period until a termination of the reaction.

U.S. Pat. No. 4,086,267 incorporates as an essential feature in the continuous oxidation of saturated aliphatic hydrocarbons with cobalt catalyst and oxygen, the feature in which a substantially gas free liquid is withdrawn from the base of the reaction zone and claims as an improvement using as the catalyst cobalt in the reaction zone in the +3 oxidation state. U.S. Pat. No. 4,131,741 claims an improved oxidation of saturated aliphatic hydrocarbons to acetic acid by limiting the residence time of the cobalt catalyst solution which is recycled so as to minimize the reduction of cobalt in the +3 oxidation state to cobalt in the +2 oxidation state.

In U.S. Pat. No. 4,131,742 a disclosure is made of the production of acetic acid by the oxidation of saturated aliphatic hydrocarbons with a cobalt catalyst in liquid phase in which a substantially gas free liquid is withdrawn from the base of the reaction zone and the reactor is fabricated from a substantially chromium-free material so that the level of chromium in the reaction medium is not greater than 400 ppm. In U.S. Pat. No. 3,196,182 an elongated reaction zone using plug flow of the reactants is used for producing oxygenated organic compounds by the liquid-phase oxidation of saturated aliphatic hydrocarbons.

U.S. Pat. No. 3,282,994 discloses a process for preparing acetic acid by the oxidation of butane which utilizes as a critical factor a reaction zone whose length to diameter ratio is less than about 15:1.

U.S. Pat. No. 3,646,128 discloses the oxidation of butane by a method which relies on using a liquid-separation zone wherein two liquid layers are obtained from the reaction zone for a work-up of the product.

U.S. Pat. No. 3,923,882 discloses the oxidation of butane in the liquid phase to provide acetic acid which utilizes ethanol as a promoter for the oxidation.

Despite the plethora of known processes for the catalytic, liquid-phase oxidation of butane to acetic acid there is still a need for a method of higher efficiency than those presently extant.

SUMMARY OF THE INVENTION

An improvement has been found in the continuous process for cobalt-catalyzed, liquid-phase oxidation of butane to acetic acid with oxygen at a pressure of about 200 to about 1000 psig. in acetic acid solvent at a temperature of about 80° to about 150° C. in the presence of an oxidation promoter wherein the cobalt catalyst stream is recycled, said improvement which comprises:

(1) keeping the iron concentration in the catalyst recycle stream below about 1000 parts per million;
(2) limiting the water concentration to a maximum of about 3% by weight in the catalyst recycle stream;
(3) maintaining a cobalt acetate concentration of at least about 0.1% but no more than 3% elemental cobalt based on the weight of the reaction mixture; and
(4) continuously removing succinic acid byproduct whereby a level below the saturation point of said succinic acid is maintained in the process streams.

Figure 2:
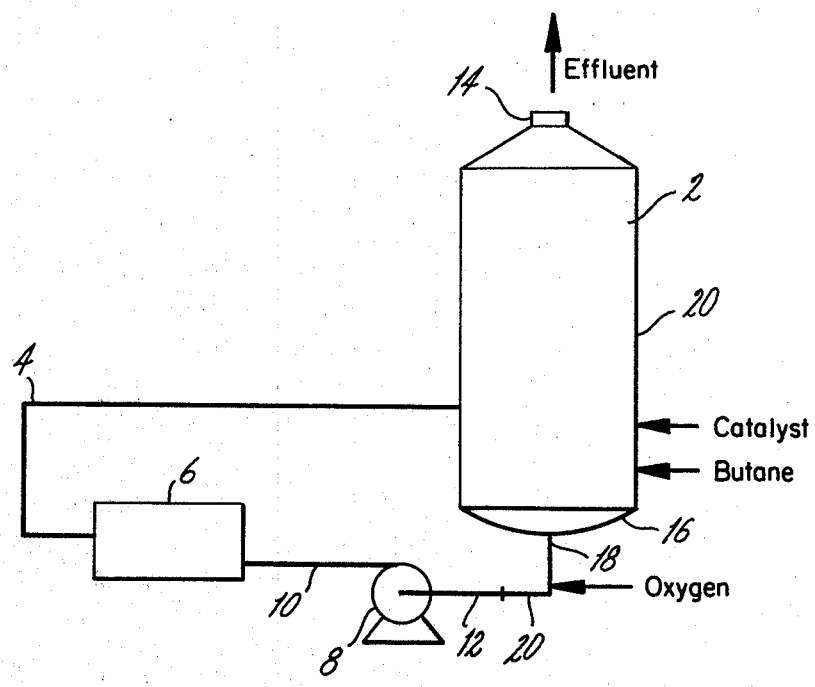
Figure 3:
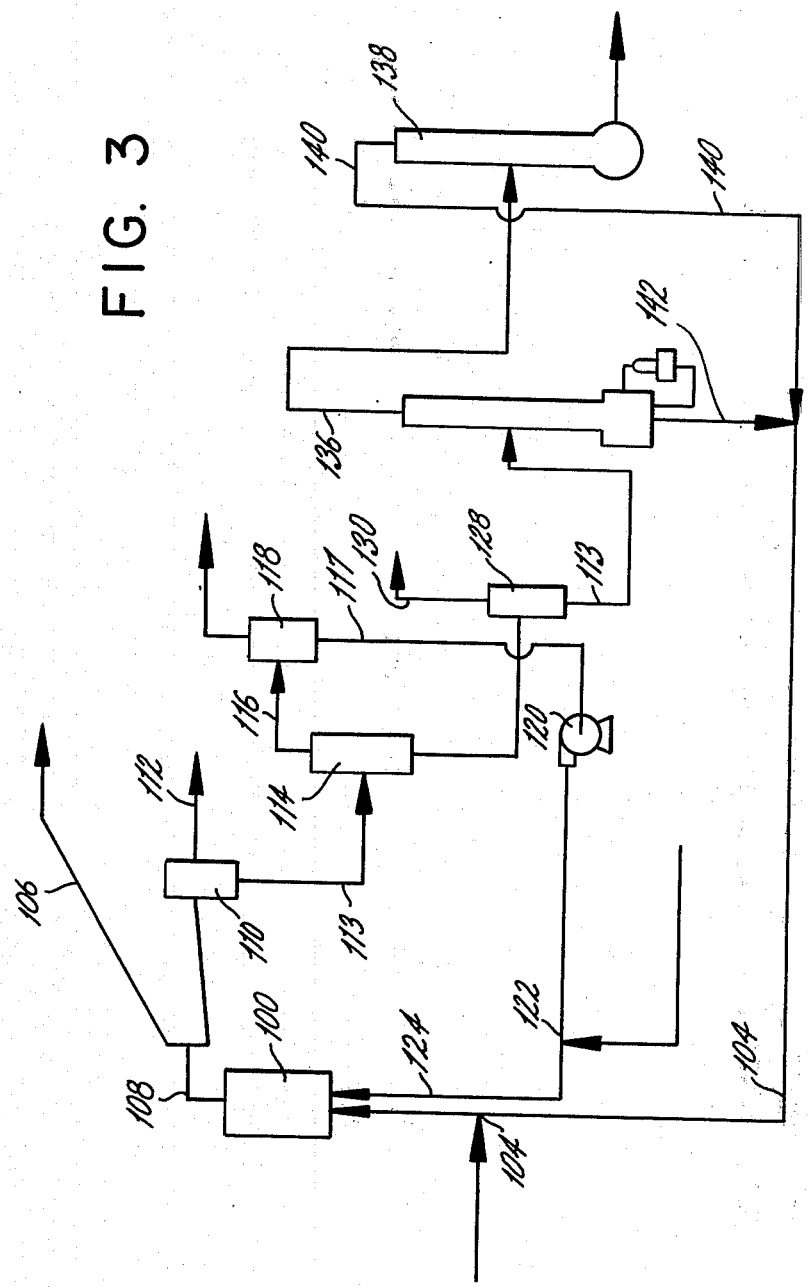

FIG. 1 is a flow diagram of the claimed invention.
FIG. 2 shows the oxidation reactor configuration.
FIG. 3 is a diagram of a pilot scale oxidation of butane.

The reactor for this process can be any suitable gas-liquid contacting reactor with means for heat removal. However, as will be understood by those skilled in the art, the productivity or efficiency of the reaction can be increased or decreased depending upon the efficiency of the mixing operation in the reactor. Inefficient mixing can result in a drop of productivity of from about $\frac{1}{2}$ to about $\frac{1}{4}$ of the desired rate. An internally agitated tank with internal cooling coils and baffles serves as a satisfactory reactor for yielding a reasonably economical rate of production of acetic acid. However, even greater economic advantages can be achieved by using a loop-circulated reactor with the coolers located in the external loop. Such a reactor is delineated in FIG. 2.

Loop-circulated reactors have been described in the literature, as for example, U.S. Pat. No. 3,846,079 which describes a gas-liquid contacting reactor with loop circulation in tangential entry of the loop. In that patent the oxidation of hydrocarbons, such as, cyclohexane in the presence of a boron catalyst is described. The tangential stirring is cited as a way of preventing particulate buildup on the walls of the reaction vessel.

The preferred practice of the invention utilizes a loop-circulated reactor with tangential stirring to enhance the oxygen absorption and hence the productivity. It is also advantageous to locate a single tangential entry device at the bottom of the reactor rather than at the top since this affords a fourfold increase in oxygen absorption, when the loop return nozzle, that is, the single tangential entry device is located there. The loop exit from the reactor is preferentially located in the reactor bottom as well. By locating the return down near the reactor bottom bypassing of unreactive oxygen from the reactor liquid phase is prevented.

FIG. 2 illustrates the above criteria but it will be understood by those skilled in the art that this is not to be an interpretation of the limitation of the scope of the invention. The reactor system contains a reactor body (2) and an external loop (4) which includes a heat removal device, such as, heat exchanger (6) which can be either gas cooled or liquid cooled. Oxygen or a gas mixture containing oxygen is fed to the loop either before or after the loop pump (8) as for example at locations (10) or (12). Oxygen can be fed to the reactor body (2) but higher productivity results with oxygen feed to the loop (4). Butane and catalyst can be fed to either the reactor body (2) or to the loop (4) and the products are continuously withdrawn from the reactor top at point (14). The dimensions of the reactor body (2) are not narrowly critical but preferably the height of the reactor body (2) should not be less than equal to the diameter and not greater than 10 times the diameter with the preferable height being equal to 1.5 to 2 times the diameter. The height of the reactor (2) depends on the loop pumping capacity needed to provide the above criteria.

The diameter of the loop piping (4) should be designed so that a turbulent flow regime is obtained inside the pipe. The loop (4) exits the reactor near the bottom (16) and returns to the reactor at a point near the reactor bottom (16). The loop exit can be located near the reactor top (14) or anywhere between the reactor top (14) and bottom (16) as long as the exit point is well below the liquid level in the reactor (2). The loop return (4) to the reactor (2) is the more important location and should be near the reactor bottom (16). If the loop exit (18) is from the reactor bottom (16) then the return (20) should be located at a point that is between about an eighth and a half of the reactor height from the reactor bottom (16). An alternative arrangement consists in distributing the loop flow in two or more return nozzles which can enter the reactor (2) at several points along the height of the reactor body the flow can be distributed equally or unequally to meet the criterion given above.

The invention is generally described in the flow diagram of FIG. 1. Butane and oxygen enter reactor (1) at points (3) and (5) and either fresh or recycled cobalt acetate catalyst at point (7). Reaction products leave the reactor at point (9) as feed (11) which splits to the vapor-liquid separator (9a) the stream into feed lines (13) and (15) the former going to exhausting column (17) from which carbon dioxide is removed at point (19) and the remainder leaves exhausting column (17) at point (21) forming stream (23) which joins stream (25). The liquid stream (15) from the separator (9a) goes to the decanter (9b) where a butane-rich stream (9c) is removed from the aqueous product stream before it goes to butane stripping still (27) and from there to catalyst recovery column (29) as stream (31). Stream (33) leaves the catalyst recovery column and proceeds to refining column (35) from which water is removed at point (37) and glacial acetic acid at point (39). The remaining stream is removed from refining column (35) at point (41) to form stream (43) which is joined by stream (45) from catalyst recovery column (29) to form stream (47) which proceeds to crystallizer (49). Succinic acid is crystallized out of the stream and removed at point (51). The reaction stream (53) then proceeds from the crystallizer minus the succinic acid removed to constitute catalyst makeup for recycle to the reactor (1) through stream (55). Butane and light by-products are recycled from decanter (9b) and butane stripping still (27) through stream (25) back to reactor (1).

CONTROL OF WATER CONCENTRATION IN THE CATALYST RECYCLE STREAM

The catalyst recovery column (29) should be operated to control the water concentration between 0.5 and 3.0 weight percent based on the weight of the catalyst recycle stream (45) with a range of about 1% to 2% being particularly desired. If the water concentration goes below 0.5% by weight, the catalyst cobalt acetate will precipitate from solution and build-up on the heating surfaces of the column. Water concentrations greater than 3% by weight will reduce the productivity in reactor (1) or cause the oxidation reaction of butane to die due to high water concentrations in the reactor which would result from a combination of the water produced in the reaction and the high water content of the recycled catalyst stream (55). The preferred upper limit of water in reactor (1) is about 20% by weight based on the weight of the mixture in the reaction zone and the optimum range for water is about 2 to about 10% by weight. At water concentrations greater than about 20% by weight in reactor (1) the dissolved butane concentration falls so low that the reaction cannot be sustained.

CONTROL OF OXYGEN CONCENTRATION IN THE REACTOR EFFLUENT

In order to ensure maximum productivity in the reactor (1), it is desirable to operate with a small amount of oxygen in the reactor effluent (11). A side stream is removed from the reactor effluent so that the butane and oxygenated products can be condensed. The remaining stream which consists of oxygen and inert gases, such as, nitrogen and carbon dioxide is measured for oxygen content by means of an oxygen measuring device. Oxygen concentrations at the analyzer should be in the range of 0.1% to 10% by weight for maximum productivity with a preferred range being from about 1% to about 8%. Below 0.1% the oxygen concentration becomes difficult to measure and control while above 10% the oxygen concentration approaches the explosive limits of oxygen in butane vapors. The oxygen concentration in the reactor effluent (11) can be controlled in several ways but the preferred way being the adjustment of the oxygen feed rate entering reactor (1) at point (5). Butane concentration in the reactor, water concentration in the reactor and temperature all affect the oxygen concentration in the reactor effluent (11).

CONTROL OF IRON CONCENTRATION IN THE CATALYST RECYCLE STREAM

It has been found that high concentrations of soluble iron salts in reactor (1) will cause the oxidation of butane to die. A stainless steel reaction system which is normally used in corrosive pilot plant operations was found to corrode in the presence of the cobalt acetate catalyst, acetic acid and oxygen at the oxidation reaction conditions. The corrosion product was a soluble iron salt which accumulated with time in the catalyst recycle stream (55) until the level became high enough to kill the oxidation reaction.

It has been found that the reaction stops when the iron concentration based on the weight of metallic iron reached between 1000 ppm and 2000 ppm in the catalyst recycle stream (55).

A preferred way to prevent iron accumulation in the catalyst recycle system is the use of titanium equipment in place of stainless steel equipment in the reactor system where stainless steel is corroded by the catalyst mixture. Other non-ferrous metals, such as, zirconium may also be used as the material of construction for the reactor (1).

Other solutions to this problem may be used such as by purging a small amount of the recycle stream for iron removal or precipitating iron salts followd by filtration. These solutions, however, are costly and uneconomical resulting in loss of the catalyst as well.

CONTROL OF SUCCINIC ACID CONCENTRATION IN THE CATALYST RECYCLE STREAM

Succinic acid is a product of the oxidation of butane and is the only by-product which cannot be recycled to extinction. Succinic acid accumulates with time in the catalyst recycle stream. While high concentrations of succinic acid have no adverse effect on the actual oxidation reaction, the concentration eventually reaches a level where the solubility limits in the catalyst recycle mixture are exceeded and precipitation of succinic acid occurs. The succinic acid precipitate results in plugging of the recycle catalyst process line, the orifice flow meter and the pumping system used to move the stream through the lines. This necessitates shutdown of the equipment and cleaning of lines and instruments which is obviously unacceptable.

Therefore, it is necessary to control the succinic acid concentration in the catalyst recycle stream at a level below its saturation point to prevent its precipitation. A crystallizer placed in the line serves this purpose. One can also purge a small amount of recycle material continuously. Heating of the catalyst recycle line will cause a higher solubility level of succinic acid in the catalyst recycle mixture and thereby allow a smaller purge rate to be used since purge rate is a function of the productivity of succinic acid in the reactor and its concentration in the purging stream.

The invention is further described in the examples which follow. All parts and percentages are by weight unless otherwise specified.

Productivity of the butane oxidation reaction is measured by the net pounds of acetic acid produced per hour divided by the reactor volume.

Since two moles of acetic acid can be made from each mole of butane, the carbon efficiency is calculated by the following expression:

$$\% \text{ carbon efficiency to acetic acid} = \frac{\text{moles of acetic acid formed} \div 2}{\text{moles butane fed} - \text{moles butane recovered}} \times 100$$

EXAMPLE 1

Using the flow diagram in FIG. 3 as a guide, liquid butane, a mixture of oxygen and nitrogen and an ethanol promoter were fed to the reactor (100) along with recycle cobalt acetate catalyst and recycle products from stream (104). The oxidation of butane was carried out in reactor (100) at a temperature of 140°–145° C. and a pressure of 500 psig. A side stream of gas (106) was removed from reactor effluent (108) for oxygen analysis and then vented. The main stream (107) from effluent (108) was cooled and passed into vapor liquid separator (110) where the carbon dioxide, nitrogen and other gases were removed through vent (112) as off gas. The liquid products from (110) were further cooled in line (113) before passing into decanter (114) where the unreacted butane was separated from the aqueous product layer which contained the cobalt acetate catalyst. Some acetic acid, water and by-products were contained in the butane-rich upper layer from the decanter (114) which mixture was recycled to the reactor through line (116) passing first through butane surge tank (118) and then through line (117) to butane recycle pump (120) from whence it combined with fresh butane at point (122) into line (124). The lower layer in decanter (114) was passed through stream (126) into butane flash pot (128) where residual butane in the lower level was flashed from the solution and vented through vent (130). The stream passed from butane flash pot (128) through stream (131) into catalyst stripping still (134) where the acetic acid, water and other compounds formed in the reaction were distilled overhead. This distillation was regulated so that the material in the base of the still (134) was a solution of cobalt acetate in acetic acid with the catalyst concentration being from 2.0 to 4.0 weight percent as cobalt acetate tetrahydrate. The overhead from the catalyst stripping still was fed through stream (136) to lights stripping still (138) where by-products of the oxidation that had a lower boiling point than acetic acid were stripped overhead and recycled through stream (140) together with the catalyst mixture from the base of the catalyst stripping still stream (142) to combine to form stream (104) leading back to reactor (100).

Table 1 delineates the operating conditions, productivities and efficiencies for six different runs. In the first four runs the promoter used was a combination of methyl ethyl ketone and ethanol. The last two runs used acetaldehyde as the promoter. The promoter feed ranged from 4.0% to 13% by weight of the catalyst recycle stream.

TABLE I
OPERATING CONDITIONS, PRODUCTIVITIES, AND EFFICIENCIES

| Operating Conditions | | | | | | |
|---|---|---|---|---|---|---|
| Reactor Temperature, °C. | 146 | 141 | 140 | 141 | 140 | 141 |
| Reactor Pressure, psig | 500 | 500 | 500 | 500 | 500 | 500 |
| Oxygen Feed, SCFH[1] | 26.9 | 26.9 | 26.7 | 24.8 | 27.6 | 26.1 |
| Butane Feed, g/hr | 1312 | 1103 | 994 | 1052 | 1072 | 1108 |
| Acetaldehyde Feed, g/hr | — | — | — | — | 281 | 114 |
| Ethanol Feed, g/hr | 70.8 | 64.7 | 67.9 | 32.7 | — | — |
| MEK Feed, g/hr | 123 | 187 | 176 | 229 | — | — |
| Butane Recycle, g/hr | 4214 | 4017 | 4835 | 5233 | 5149 | 5123 |
| Catalyst Recycle, g/hr | 2960 | 1929 | 2094 | 2427 | 2509 | 2651 |
| Productivities - lb/ft³/hr | | | | | | |
| Acetic Acid | 9.62 | 12.06 | 11.40 | 9.33 | 13.53 | 11.81 |
| Propionic Acid | 0.25 | 0.29 | 0.35 | 0.23 | 0.36 | 0.25 |
| Butyric Acid | 0.06 | 0.07 | 0.13 | 0.05 | 0.15 | 0.07 |
| Water | 3.89 | 3.48 | 3.76 | 2.50 | 3.44 | 3.56 |
| Carbon Dioxide | 2.25 | 3.04 | 2.92 | 2.89 | 3.83 | 2.70 |
| Carbon Efficiencies - % | | | | | | |
| Acetic Acid | 78.97 | 77.96 | 75.80 | 74.72 | 77.13 | 78.14 |
| Propionic Acid | 2.52 | 2.26 | 2.81 | 2.24 | 2.52 | 2.01 |
| Butyric Acid | 0.70 | 0.60 | 1.17 | 0.53 | 1.14 | 0.64 |
| Other Liquids | 2.57 | 2.21 | 3.89 | 2.82 | 1.15 | 4.64 |
| Carbon Monoxide | 2.64 | 3.57 | 3.06 | 3.92 | 3.17 | 2.37 |
| Carbon Dioxide | 12.60 | 13.40 | 13.27 | 15.77 | 14.89 | 12.20 |

[1]Standard cubic feet/hour

CONTROL A

This example illustrates the importance of controlling the water concentration in the catalyst recycle stream. The procedure used in Example 1 was followed except that only catalyst was recycled to the reactor and ethanol was used as the promoter. The run conditions were as follows:

| | |
|---|---|
| Reactor Temperature, °C. | 140 |
| Reactor Pressure, psig | 500 |
| Oxygen Feed, SCFH | 22 |
| Butane Feed, g/hr | 2380 |
| Ethanol Feed, g/hr | 55 |

| -continued |   |
| --- | --- |
| Catalyst Recycle, g/hr | 2500 |

The reactor was started up and lined-out with fresh catalyst feed at a rate equivalent to the above recycle catalyst rate in Example 1. The reactor water concentration was 7.5%. When the catalyst stripping still was lined-out, the recycle catalyst was started at the above rate. The recycle catalyst was estimated to have 4% water. The reactor water concentration increased to 10.7%. The catalyst stripping still was operated on total reflux for one hour which greatly increased the water concentration in the recycle stream. 2.5 hours later the reaction died. The water content of the reactor was 11.1%. It may be concluded that the high water concentration of the catalyst recycle stream had caused the reactor water concentration to become too high and killed the reaction.

To further illustrate the importance of water concentration in catalyst feed to the reactor, the unit was operated single pass. The reactor was charged with the following mixture: 3500 milliliters of a 3.5% solution of cobaltous acetate tetrahydrate and 2.0% ethanol in acetic acid, 300 milliliters of ethanol, 125 milliliters of water and 4.0 pounds of butane. The water addition amounted to 3.0 weight percent of the catalyst solution and along with the 37 milliliters of water that were part of the cobaltous acetate tetrahydrate molecule, increased the total water content of the catalyst solution to 4.0 weight percent. The reactor was heated to about 140° C. after the pressure had been raised to 500 psig with nitrogen. While the pressure was maintained at 500 psig, 225 liters per hour of nitrogen were fed and oxygen was admitted at the rate of 120 liters per hour. The oxidation reaction could not be initiated as indicated by the high oxygen concentrations in the reactor effluent. Several attempts were made at initiating the reaction but all were unsuccessful.

CONTROL B

This run illustrates the importance of controlling the iron salt concentration in the catalyst recycle stream.

The pilot unit used was operated as described in Example 1. For this run, the reactor was constructed of 316L stainless steel. The pilot unit equipment was thoroughly cleaned and all lines and tanks were empty prior to starting the experiment. To start the reaction, the reactor was charged with 5000 milliliters of a 3.5 percent solution of cobaltous acetate tetrahydrate in acetic acid, 200 milliliters of ethanol, 300 milliliters of methyl ethyl ketone and 4.5 pounds of butane. The pressure was raised to 500 psig with nitrogen and the mixture was heated to about 140° C. While the pressure was maintained at 500 psig, 225 liters per hour of nitrogen were fed and oxygen was admitted at the rate of 120 liters per hour. The reaction started within about three minutes at which time the oxygen rate was increased in small increments until the oxygen concentration in the stream passing through the oxygen analyzer was at least 2.0%.

When the reaction started, the butane feed was started at 4.5 lbs/hr and a solution of 1.75% cobaltous acetate tetrahydrate and 2.0% ethanol in acetic acid was fed at the rate of 2500 milliliters per hour.

As the operation proceeded the reactor was filled and the effluent overflowed through a condenser to the vapor-liquid separator where the carbon dioxide and nitrogen along with some butane were removed. When the vapor-liquid separator was about ⅔ full with liquid, the liquid level motor valve was activated by the liquid level controlling instrument and the liquid passed through the motor valve and through a cooler to the decanter where the unreacted butane separated from the aqueous catalyst phase. The upper, butane rich phase in the decanter overflowed into the butane surge tank when the decanter became full. When the butane surge tank became two-thirds full the butane recycle pump was started which pumped the butane rich phase from the decanter into the reactor. The butane recycle was started at 7.5 lb/hr about one hour after the reaction started.

The lower layer interface in the decanter was controlled by means of a differential pressure meter, a controller and a motor valve. The lower layer passed through the motor valve where the pressure was reduced from about 425 psig to atmospheric pressure. The liquid passed into the butane flash pot where any residual butane in the liquid was flashed from solution and vented. When the flash tank became about two-thirds full, the catalyst stripping still feed pump was started and the flash tank liquid was pumped into the catalyst still at a rate of 3500 milliliters per hour. When the still kettle was full, the kettle heater was activated and the distillation began. The tails from the still were monitored for water concentration so that when the water concentration reached a level between 1 and 2%, the tails were collected in the catalyst recycle tank. When the recycle tank was about two-thirds full, the recycle pump was started and the accumulated tails material, which contained the catalyst, was recycled to the reaction at the rate of about 2500 milliliters per hour. The fresh catalyst feed was terminated and the ethanol feed was started at about 60 milliliters per hour.

The overhead from the catalyst stripping still was collected in the lights stripping still feed tank. When the tank was about two-thirds full, the lights still feed pump was started and the material was fed to the still at a rate of about 1000 milliliters per hour. This feed rate was adjusted to maintain a constant level in the feed tank. When the lights still kettle was full, the kettle heater was activated and the distillation was begun. The product was removed from the kettle at a rate that was sufficient to maintain a constant level in the kettle. The overhead from the still which contained the light by-products that were formed in the reaction was combined with the catalyst recycle for feeding to the reactor.

As the above operation proceeded, the iron concentration of the catalyst recycle material was monitored. The results were as follows:

| Time - Hours | Iron, ppm | Remarks |
| --- | --- | --- |
| 0 | 0 | Reaction started |
| 10 | 350 | Catalyst recycle started |
| 30 | 900 |  |
| 35 | 1000 |  |
| 44 | 1180 | Reaction died |

The results show that the iron was accumulating in the catalyst recycle with time and caused the reaction to die.

CONTROL C

This run illustrates the importance of controlling the succinic acid concentration in the catalyst recycle stream.

The pilot unit used was operated as described in Example 1. After 100 hours of operation, the catalyst recycle flow was retarded by crystalline succinic acid which had precipitated from solution in the recycle catalyst pump and orifice meter. The succinic acid was accumulating in the catalyst recycle stream because it was not being oxidized in the reactors at the rate at which it was being produced. Plugging of the catalyst recycle line was first noticed after 100 hours of operation with catalyst recycle. The succinic acid concentration at this time was greater than 4.0 weight percent. Plugging problems continued until a batch crystallizing tank was installed at 160 hours of operation with catalyst recycle. The crystallizer successfully reduced the succinic acid concentration below 4.0 weight percent and the plugging problems were eliminated until the crystallization tank was removed.

Although the invention has been described in its preferred forms with a certain degree of particularity, it is understood that the present disclosure of the preferred forms has been made only by way of example and that numerous changes may be resorted to without departing from the spirit and the scope of the invention.

What is claimed is:

1. In a continuous process for the cobalt catalyzed liquid-phase oxidation of butane to acetic acid with oxygen at a pressure of about 200–1000 psig in acetic acid solvent at a temperature of about 80°–150° C. in the presence of an oxidation promoter wherein the cobalt catalyst stream is recycled, the improvement which comprises:
   (1) keeping the iron concentration below about 1000 parts per million in the catalyst recycle stream;
   (2) limiting the water concentration to a maximum of about 3% based on the weight of the catalyst recycle stream;
   (3) maintaining a cobalt acetate concentration of at least about 0.1% but no more than 3% based on the weight of the reaction mixture; and
   (4) continuously removing succinic acid by-product whereby a level below the saturation point of succinic acid is maintained in the reaction media.
2. Process claimed in claim 1 wherein the temperature is about 140°–145° C.
3. Process claimed in claim 1 wherein the pressure is in the range of about 300 to about 500 psig.
4. Process claimed in claim 1 wherein the cobalt acetate concentration is in the range of about 2 to about 3.0% by weight of the reaction mixture.
5. Process claimed in claim 1 wherein the amount of butane used in the reaction based on the weight of the solvent is in the range of about 50% to about 125%.

* * * * *